United States Patent [19]

St. Clair et al.

[11] Patent Number: 5,220,070
[45] Date of Patent: Jun. 15, 1993

[54] 1,3-DIAMINO-5-PENTAFLUOROSULFA-NYLBENZENE

[75] Inventors: Terry L. St. Clair; Anne K. St. Clair, both of Poquoson; Joseph S. Thrasher, Tuscaloosa

[73] Assignee: The United States of America as represented by the Administrator National Aeronautics and Space Administration, Washington, D.C.

[21] Appl. No.: 755,207

[22] Filed: Sep. 5, 1991

[51] Int. Cl.$^5$ ............................................. C07C 323/09
[52] U.S. Cl. ..................................... 564/440; 564/417; 562/827
[58] Field of Search .......................... 564/440; 562/827

Primary Examiner—Richard L. Raymond
Attorney, Agent, or Firm—George F. Helfrich

[57] ABSTRACT

A process was developed to prepare 1,3-diamino-5-pentafluorosulfanylbenzene. This process involved two steps: preparing the dinitro compound, 1,3-dinitro-5-pentafluorosulfanylbenzene, and reducing this compound to form the corresponding diamine. This diamine was reacted with various dianhydrides, diacidchlorides, and epoxy resins to form polyimides, polyamides, and crosslinked epoxies. These polymers were used to prepare semi-permeable membranes, wire coatings, and films.

1 Claim, No Drawings

1,3-DIAMINO-5-PENTAFLUOROSULFANYLBENZENE

ORIGIN OF THE INVENTION

The invention described herein was jointly made by employees of the United States Government and a contract employee in the performance of work under NASA Grant No. NAG1-1069 and is subject to the provisions of Public Law 96-517 (35 USC 202) in which the contractor has elected not to retain title.

BACKGROUND OF THE INVENTION

1. Field of the Invention

The present invention relates to a process for preparing a diamine. It specifically relates to a process for preparing a diamine which contains a pentafluorosulfanylbenzene moiety.

2. Description of Related Art

Diamines have shown their utility in the formation of many polymers. Examples of these polymers include polyimides, polyamides, and epoxies. The properties of these polymers are often dependent on the diamine which is used to make the polymer. By the present invention, a process was developed to make a diamine containing a pentafluorosulfanylbenzene moiety.

SUMMARY OF THE INVENTION

The diamine, 1,3-diamino-5-pentafluorosulfanylbenzene (DASP), was prepared and has the structural formula:

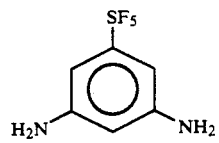

A new process was developed in order to prepare this diamine. This process involves two steps: the preparation of a dinitro precursor and the reduction of the dinitro compound to form the diamine.

The dinitro compound was prepared by reacting silver fluoride with bis(3,5-dinitrophenyl)disulfide. The mixture was evacuated and a chlorinated fluorocarbon was added. The reaction was gradually heated to 130° C. and this temperature was maintained for two hours. The reactor was cooled to room temperature and the chlorinated fluorocarbon was removed under vacuum. The product was extracted and distilled under vacuum. The resulting yellow oil was further purified by high pressure liquid chromatography (HPLC) and the dinitro product precipitated. The product, 1,3-dinitro-5-pentafluorosulfanylbenzene, was filtered and dried.

The 1,3-dinitro-5-pentafluorosulfanylbenzene was mixed with absolute ethanol, chloroform, concentrated hydrochloric acid, and a catalyst. The reaction mixture was pressurized with hydrogen gas, filtered and distilled to form a crude amine hydrochloride. The amine hydrochloride was neutralized and a non-water soluble organic solvent was added to form a separate phase containing the diamine. This phase was separated and dried, forming a solid. The solid was recrystallized to give the diamine, DASP.

This diamine monomer (DASP) was combined with the following dianhydrides to form the corresponding polyimide polymers.

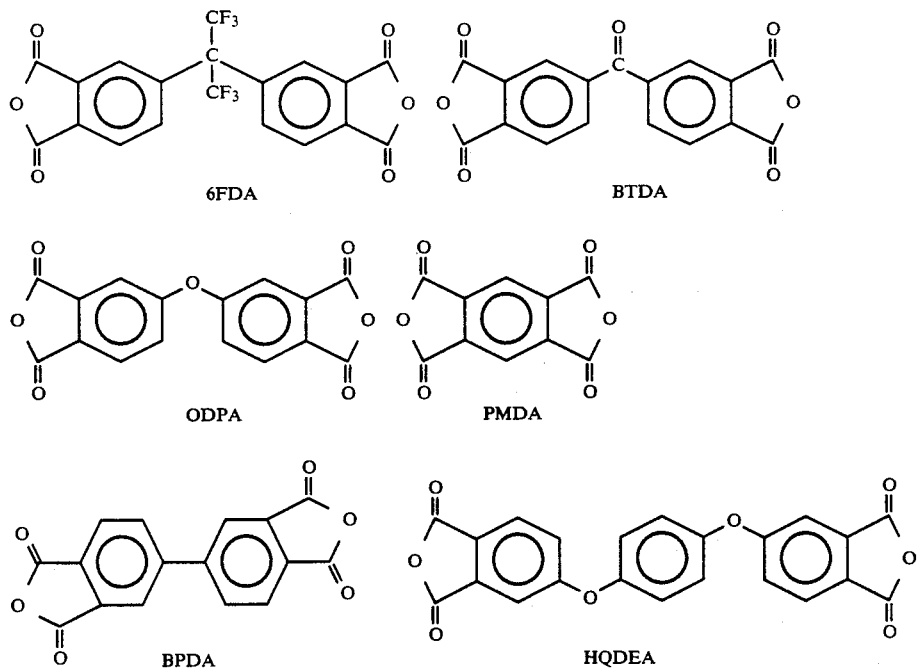

-continued

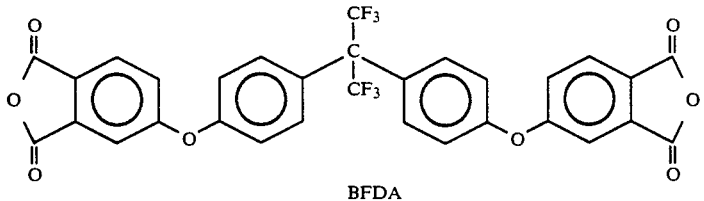

BFDA

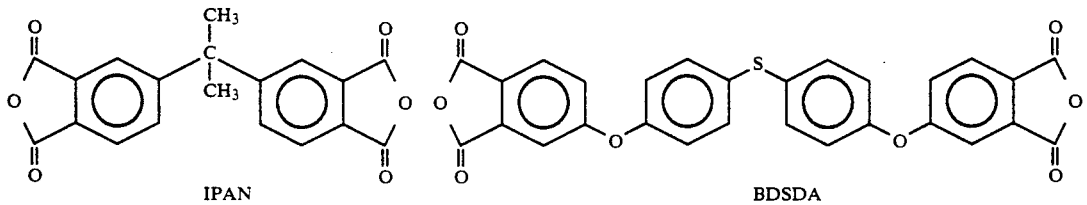

IPAN                                BDSDA

DASP was also reacted with the following diacid-chloride to form the corresponding polyamide.

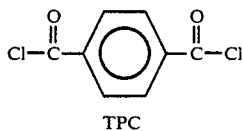

TPC

A crosslinked epoxy polymer was formed by reacting DASP with the liquid epoxy resin, MY-720 ®, available commercially from Ciba-Geigy and having the structure:

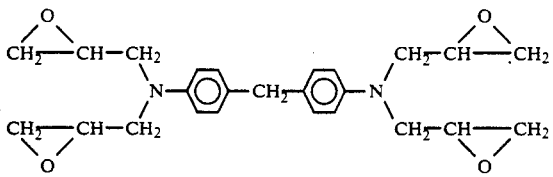

Several articles were prepared from these polymers. These articles include: semi-permeable membranes, wire coatings, and films.

An object of the present invention is to develop a process to make 1,3-diamino-5-pentafluorosulfanylbenzene.

Another object of the present invention is to make polymers with the diamine, 1,3-diamino-5-pentafluorosulfanylbenzene.

Another object of the present invention is to make articles from the polymers.

Description of the Preferred Embodiments

EXAMPLE 1

A 1000 ml capacity stainless steel reactor, tested at 60 p.s.i. pressure and pre-treated with fluorine, was charged with 165 g of silver fluoride ($AgF_2$), 30 g of bis(3,5-dinitrophenyl)disulfide, ten copper sheets (0.1×15×60 mm), and then an additional 150 g of $AgF_2$. The reactor was evacuated on a vacuum line, and 200 ml of 1,1,2-trichlorotrifluoroethane was added while maintaining the reactor at −80° C. The reactor was shaken for 5 minutes, warmed to room temperature, and then placed in an oil bath and heated to 60° C.

After two hours at 60° C. gradually increased over 30 minutes to 130° C. During a two hour period at 130° C., the reactor was shaken at 30 minute intervals for 5 minutes. The reactor was then cooled to room temperature, and the 1,1,2-trichlorotrifluoroethane was removed under vacuum. The product was extracted from the reaction mixture three times with 150 ml portions of carbon tetrachloride ($CCl_4$) and two times with 150 ml portions of trichloromethane ($CHCl_3$).

The extracts were combined and the $CCl_4$ and $CHCl_3$ were distilled off under vacuum. The resulting residue, a yellow oil (25.6 g), was further purified by HPLC using Lichroprep RP-18 ® packing, which is commercially available, and a water-methanol (1:1) mixture as eluent. The volume of the fractions containing 1,3-dinitro-5-pentafluorosulfanylbenzene was reduced in half whereupon the product precipitated. The solid product (3.1 g, 7.0% yield) was filtered and dried. The structure of the compound was confirmed by $^1H$, $^{19}F$, and $^{13}C$ NMR spectroscopy, mass spectrometry, and elemental analysis.

1,3-$(NO_2)_2$-5-$SF_5$-$C_6H_3$: mp 73°-75° C.; $^1H$ NMR δ 9.25 (t,J=1.7 Hz, 1H), 8.96 (d,J=1.7 Hz, 2H); $^{19}F$ NMR (ab$_4$ pattern) δ$_a$ 77.6 (m), δ$_b$ 62.7 (d of m) ($J_{AB}$=152.4 Hz); $^{13}C$ NMR δ C-1=C-3 148.5, C-2 121.7, C-4=C-6 126.7 (quintet, $J_{SF4-C}$=4.8 Hz), C-5 154.6 (quintet, $J_{SF4-C}$=21.5 Hz). Mass Spectrum (70 eV) m/e (rel. intensity) 294 M+ (100.0), 275 [M-F]+ (20.9), 248 [M-$NO_2$]+(28.4), 218 [M-$N_2O_3$]+ (34.3), 202 [M-$N_2O_4$]+ (13.9), 201 (94.5), 167 [M-$SF_5$]+ (10.7), 127 $SF_5$+ (3.8).

Anal.—Calcd. for $C_6H_3F_5N_2O_4S$ (294.2): C, 24.50; H,1.03; N, 9.52; S, 10.90. Found: C, 24.75; H, 1.05; N, 9.53; S, 10.64.

The 1,3-Dinitro-5-pentafluorosulfanylbenzene (4.43 g, 15.1 mmol) was combined with 100 ml absolute ethanol, 10 ml chloroform, 2.65 g of 41.59% hydrochloric acid (HCl) in ethanol, and 2.65 g platinum oxide ($Pt_2O$) and were placed in a 500 ml pressure bottle for use on a Parr hydrogenation apparatus. The system was flushed, pressurized to 100 p.s.i. with hydrogen, and shaken.

Within 1 hour the theoretical amount of hydrogen was absorbed. After filtration through Celite ®, which is commercially available from Johns-Manville Products Corporation, on a Büchner funnel, the volatile materials were distilled off at room temperature. The resulting solid (crude amine hydrochloride, 5.43 g) was then neutralized in a 500 ml separatory funnel with 60 ml of a 10% sodium carbonate ($Na_2CO_3$) solution which was covered with 20 ml of diethyl ether. After neutralization, the ether phase was separated and the water phase was extracted three times with 20 ml aliquots of ether. The combined ether extracts were dried over magnesium sulfate (MgSO₄), and the ether was evaporated. The resulting solid (3.3 g) was recrystallized from an ether-hexane mixture to give the desired product as a pale yellow solid (2.95 g, 12.6 mmol) in 83.4% yield. The structure of the compound, 1,3-diamino-5-pentafluorosulfanylbenzene (DASP), was confirmed by $^1$H, $^{19}$F, and $^{13}$C NMR spectroscopy, mass spectrometry, and elemental analysis.

1,3-$(NH_2)_2$-5-$SF_5$-$C_6H_3$: mp 153°-154° C.; $^1$H NMR δ 6.46 (d, J=1.7 Hz, 2H), 6.07 (t, J=1.7 Hz, 1H); $^{19}$F NMR (ab₄ pattern) $δ_a$ 85.2 (m), $δ_b$ 61.6 (d of m) ($J_{AB}$=149.8 Hz); $^{13}$C NMR δ C-1=C-3 147.4, C-2 103.5, C-4=C-6 103.3 (quintet, $J_{SF_4-C}$=4.8 Hz), C-5 155.9 (quintet $J_{SF_4-C}$=20 Hz). Mass spectrum (70 eV) m/e (rel. intensity) 234 M+ (100.0), 206 (3.9), 126 (6.8), 107 [M-SF₅]+ (63.5).

Anal.—Calcd. for $C_6H_7F_5N_2S$ (234.2): C, 30.77; H, 3.01; N, 11.96; S, 13.69. Found: C, 30.73; H, 3.04; N, 11.70; S, 13.56.

Although 1,1,2-trichlortrifluoroethane was used in this reaction other chlorinated fluorocarbons known to those skilled in the art can also be used.

Although platinum oxide was the catalyst used in this reaction, palladium on charcoal (Pd/C) may also be used.

Although diethyl ether was the solvent used to separate the diamine, any non-water soluble organic solvent known to those skilled in the art may be used.

EXAMPLE 2

A polyimide polymer was prepared by dissolving 0.1405 g (0.6 mmole) of DASP into 1.6282 g of N,N-dimethylacetamide (DMAc) in a ¼ oz. snap-cap jar. Next was added 0.2719 g (0.6 mmole) of 6FDA and the mixture was allowed to stir/react over a 23 hour period. The resulting yellow solution had an inherent viscosity (at 0.5% concentration in DMAc at 35° C.) of 0.35 dL/g indicating a high degree of polymerization. A thin film was cast from the solution and was cured to 300° C. The resulting polyimide polymer had the following structural formula:

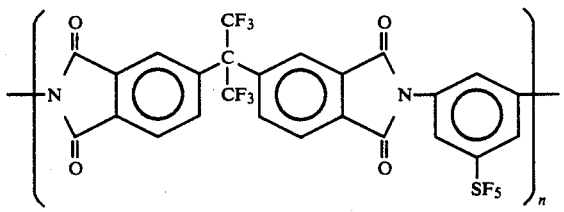

where n=10-100.

EXAMPLE 3

A polyimide polymer was prepared by dissolving 0.1124 g (0.48 mmole) DASP into 1.6563 g of DMAc in a ¼ oz. snap-cap jar. Next, 0.3017 g (0.48 mmole) of BFDA was added and the solution was allowed to stir for approximately 2 hours. An additional 0.0030 g of BFDA (1 molar percent excess) was added and the solution was stirred overnight. A pale yellow solution resulted which had an inherent viscosity of 0.44 dL/g indicating a high degree of polymerization. A thin film was cast from the solution and was cured to 300° C. The resulting polymer had the following structural formula:

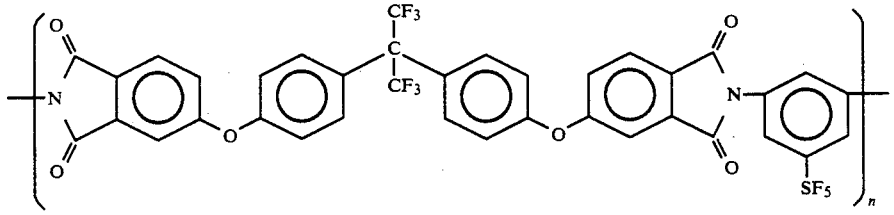

where n=10-100.

EXAMPLE 4

A polyimide polymer was prepared by dissolving 0.1850 g (0.79 mmole) DASP into 1.6698 g of DMAc in a ¼ oz. snap-cap jar. Next, 0.2348 g (0.80 mmole) of BPDA was added and the mixture was allowed to stir for approximately 24 hours. A yellow solution resulted which was found to have an inherent viscosity of 0.44 dL/g. A thin film was cast from the solution and was cured to 300° C. The resulting polymer had the following structural formula:

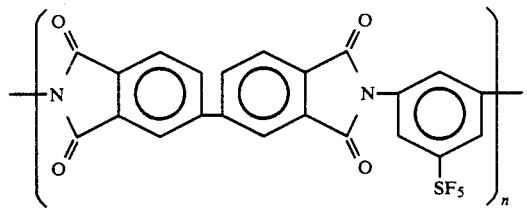

where n=10-100.

EXAMPLE 5

A polyimide polymer was prepared by dissolving 0.1756 g (0.75 mmole) DASP into 1.6332 g of DMAc in a ¼ oz. snap-cap jar. Next, 0.2350 g (0.76 mmole) of ODPA was added and the mixture was allowed to stir overnight. Another one mole percent of ODPA was added and stirring continued for approximately 4 hours. The resulting solution had an inherent viscosity of 0.48 dL/g. A thin film of this solution was cast and was cured to 300° C. The resulting polymer had the following structural formula:

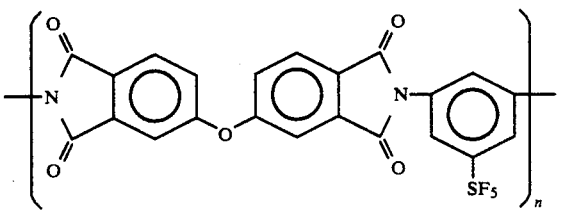

where n=10-100.

EXAMPLE 6

A polyimide polymer was prepared by dissolving 0.2108 g (0.9 mmole) of DASP into 1.6283 g of DMAc in a ¼ oz. snap-cap jar. Once the solution was attained, 0.1983 g (0.909 mmole) of PMDA was added and stirring was continued overnight. The resulting solution had a pale yellow color and an inherent viscosity of 0.36 dL/g. A thin film of this solution was cast and was cured to 300° C. The resulting polymer had the following structural formula:

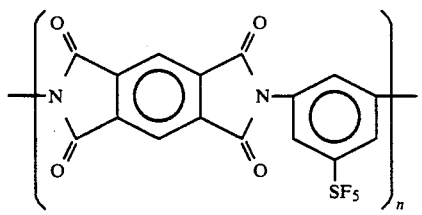

where $n = 10-100$.

EXAMPLE 7

A polyimide polymer was prepared by dissolving 0.1710 g (0.73 mmole) of DASP into 1.6658 g of DMAc in a ¼ oz. snap-cap jar. Next, 0.2480 g (0.737 mmole) of IPAN was added and the mixture was allowed to stir. After approximately 18 hours, the viscosity appeared to be low so 0.0025 g of IPAN was added to total 0.7446 mmoles of IPAN. After stirring for approximately 4 additional hours, the polymer solution was found to have an inherent viscosity of 0.38 dL/g. A thin film of this solution was cast and was cured to 300° C. The resulting polymer had the following structural formula:

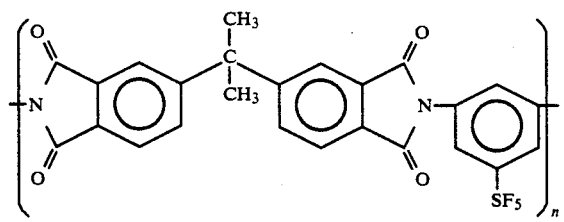

where $n = 10-100$.

EXAMPLE 8

A polyimide polymer was prepared by dissolving 0.1733 g (0.74 mmole) of DASP into 1.647 g of DMAc in a ¼ oz. snap-cap jar. Next, 0.2408 g (0.747 mmole) of BTDA was added and the mixture was stirred overnight. The resulting solution had an inherent viscosity of 0.40 dL/g. A thin film was cast from this solution and was cured to 300° C. The resulting polymer had the following structural formula:

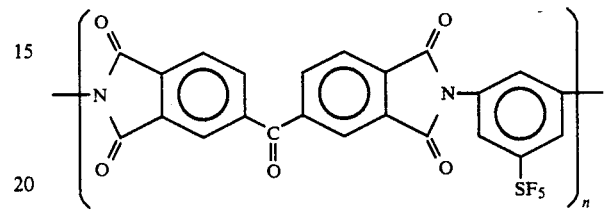

where $n = 10-100$.

EXAMPLE 9

A polyimide polymer was prepared by dissolving 0.1499 g (0.64 mmole) of DASP into 1.6295 g of DMAc in a ¼ oz. snap-cap jar. Next, 0.2601 g (0.646 mmole) of HQDEA was added and the mixture was stirred for approximately 20 hours. The resulting pale yellow solution had an inherent viscosity of 0.40 dL/g. A thin film of this solution was cast and was cured to 300° C. The resulting polymer had the following structural formula:

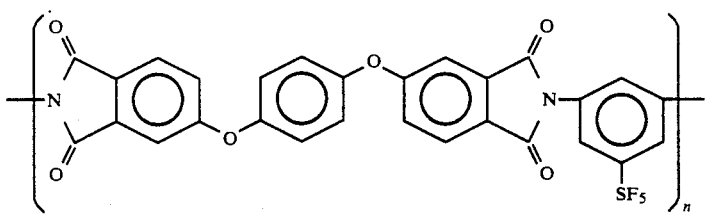

where $n = 10-100$.

EXAMPLE 10

A polyimide polymer was prepared by dissolving 0.1288 g (0.55 mmole) of DASP into 1.6383 g of DMAc in a ¼ oz. snap-cap jar. Next, 0.2836 g (0.5555 mmole) of BDSDA was added and the mixture was allowed to stir overnight. This solution had an inherent viscosity of 0.45 dL/g. A thin film of this solution was cast and was cured to 300° C. The resulting polymer had the following structural formula:

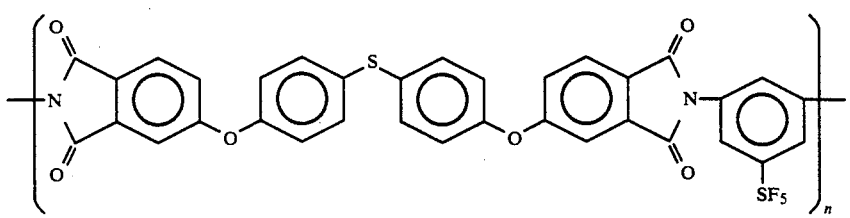

where n=10-100.

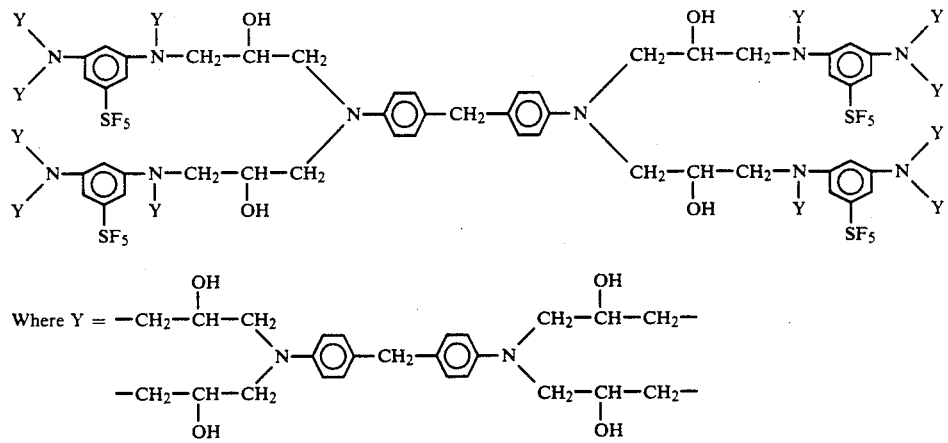

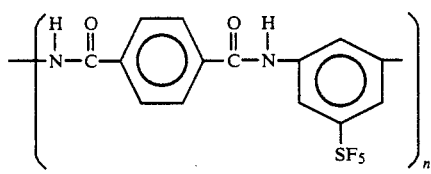

EXAMPLE 11

A polyamide polymer was prepared by mixing equimolar amounts (0.5 mmole) of DASP and terephthaloylchloride in 2 ml of DMAc and allowing the solution to stir overnight. A yellow solution resulted which had an inherent viscosity of 0.58 dL/g. A thin film of this solution was cast and was cured to 200° C. The polyamide film was clear, colorless and flexible and had a dielectric constant of 3.44 at 10 GHz. The resulting polyamide had the following structural formula:

where n=10-100.

EXAMPLE 12

An epoxy resin was cured with DASP by mixing equimolar amounts (0.5 mmole) of DASP with the tetraglycidylmethylenedianiline (tetrafunctional epoxide, MY-720® available from Ciba-Giegy). The mixture was warmed to >125° C. on a hot plate and a cured or crosslinked epoxy resin resulted. The resulting crosslinked resin had the following structure:

EXAMPLE 13

A semi-permeable membrane was formed from the polymer solution of Example 3. The solution was coated onto a piece of plate glass. Next, the DMAc was allowed to evaporate at room temperature for ½ hour. The remainder of the DMAc was leached from the film by immersing it in methanol to form a membrane which was subsequently thermally treated to 200° C. to form a stable polyimide semi-permeable membrane. Although the polyimide solution of Example 3 was used to make the membrane, the polyamide and epoxy polymers could also be used.

EXAMPLE 14

A wire coating was prepared by immersing a piece of copper wire in the polymer solution from Example 3. Upon removal from the solution, the coating was allowed to air dry for approximately ½ hour. After drying, the wire was placed in an air oven at 200° C. for one hour to cure the polyimide coating. The coating on the copper wire was flexible and resisted abrading. Although the polyimide solution of Example 3 was used to make the membrane, the polyamide and epoxy polymers could also be used.

What is claimed as new and desired to be secured by Letters Patent of the United States is:

1. The diamine 1,3-diamino-5-pentafluorosulfanylbenzene.

* * * * *